(12) United States Patent
Watanabe et al.

(10) Patent No.: US 9,067,950 B2
(45) Date of Patent: Jun. 30, 2015

(54) PROCESS FOR PRODUCING SPIROGLYCOL

(75) Inventors: Masafumi Watanabe, Okayama (JP);
Junichi Amemiya, Okayama (JP);
Ikutaro Kuzuhara, Okayama (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 887 days.

(21) Appl. No.: 13/081,353

(22) Filed: Apr. 6, 2011

(65) Prior Publication Data

US 2011/0184193 A1 Jul. 28, 2011

Related U.S. Application Data

(63) Continuation of application No. 11/130,122, filed on May 17, 2005.

(30) Foreign Application Priority Data

May 19, 2004 (JP) .................................. 2004/148977

(51) Int. Cl.
*C07D 493/10* (2006.01)

(52) U.S. Cl.
CPC ..................................... *C07D 493/10* (2013.01)

(58) Field of Classification Search
None
See application file for complete search history.

(56) References Cited

U.S. PATENT DOCUMENTS

| | | | |
|---|---|---|---|
| 2,853,495 A | 9/1958 | Ruskin et al. | |
| 3,092,640 A | 6/1963 | Mantell et al. | |
| 3,935,274 A | 1/1976 | Jacobsen et al. | |
| 5,424,053 A | 6/1995 | Bauer | |
| 5,698,717 A | 12/1997 | Iyama et al. | |
| 6,143,929 A | 11/2000 | Kessel et al. | |
| 6,252,361 B1 | 6/2001 | Fernsler | |
| 6,294,693 B1 | 9/2001 | Asakawa et al. | |

FOREIGN PATENT DOCUMENTS

| | | | |
|---|---|---|---|
| JP | 59-148776 | | 8/1984 |
| JP | 3-27384 | | 2/1991 |
| JP | 04-145044 | | 5/1992 |
| JP | 04-334359 | | 11/1992 |
| JP | 07-215980 | | 8/1995 |
| JP | 7-215980 A | * | 8/1995 |
| JP | 2000-044569 | | 2/2000 |
| JP | 2000-044569 A | * | 2/2000 |
| JP | 2000-044570 | | 2/2000 |
| JP | 2001-055388 | | 2/2001 |
| JP | 2001055388 | * | 2/2001 |
| JP | 2001-302673 | | 10/2001 |
| JP | 2005-29563 | | 2/2005 |
| WO | WO 92/21645 | | 12/1992 |
| WO | WO 03/091195 | | 11/2003 |

OTHER PUBLICATIONS

European Search Report dated Sep. 30, 2005, for Application No. 05104106.9-2117 PCT.
Kubota, et al., "Seeding effect on product crystal size in batch crystallization" *Journal of Chemical Engineering of Japan*, vol. 35, No. 11, 2002, pp. 1063-1071.
Sharratt, P. N. *Handbook of Batch Process Design*, Chapman and Hall, 1997, pp. 295 and 296.
Van Zyl, et al., "Synthesis of a Series of Derivatives of Ethyl 2-Pyridylacetate", *Journal of Organic Chemistry*, vol. 26, No. 9, 1961, pp. 3373-3375.
Japanese Official Action dated Jun. 16, 2010, for JP Application No. 2004-148977.
F. R. Galiano, et al., "Formation of 1,3-Dioxanes in Water", *Journal of Organic Chemistry*, vol. 29, No. 11, 1964, pp. 3424-3426.

* cited by examiner

*Primary Examiner* — David K O Dell
(74) *Attorney, Agent, or Firm* — Greenblum & Bernstein, P.L.C.

(57) ABSTRACT

In the production of spiroglycol by the reaction of pentaerythritol and hydroxypivalaldehyde in water in the presence of an acid catalyst, (A) a total content of amines and amine salts in hydroxypivalaldehyde is reduced to 1.5% by weight or lower; (B) seed crystals are added to the reaction system before initiating the reaction and/or during the reaction in an amount from 1.5 to 30% by weight on the basis of the total feed amount of pentaerythritol, hydroxypivalaldehyde, water, the acid catalyst and the seed crystals, each being fed into the reaction system; (C) the pH of the reaction system is kept from 0.1 to 4.0 from initiation of the reaction to completion of the reaction; and (D) the sum of a maximum theoretical amount of spiroglycol to be synthesized from pentaerythritol and hydroxypivalaldehyde to be fed into the reaction system and an amount of spiroglycol contained in the seed crystals to be added to the reaction system is controlled within a range from 5 to 35% by weight on the basis of the total feed amount. The spiroglycol produced has an increased particle size. By washing the spiroglycol with a basic solution, the heat stability is improved.

12 Claims, No Drawings

PROCESS FOR PRODUCING SPIROGLYCOL

This application is a Continuation application of prior Application Ser. No. 11/130,122, filed May 17, 2005, the contents of which are incorporated herein by reference in their entirety.

BACKGROUND OF THE INVENTION

1. Field of the Invention

The present invention relates to a process for producing high-purity 3,9-bis(1,1-dimethyl-2-hydroxyethyl)-2,4,8,10-tetraoxaspiro[5.5]undecane (hereinafter referred to merely as "spiroglycol" or "SPG") which is mainly usable as a raw material of resins.

2. Description of the Prior Art

Spiroglycol is produced, for example, through the steps of conducting an acetalization reaction of hydroxypivalaldehyde (hereinafter occasionally referred to merely as "HPA") and pentaerythritol (hereinafter occasionally referred to merely as "PE") in water in the presence of an acid catalyst, neutralizing with alkali, removing spiroglycol crystals precipitated during the reaction by filtration, washing with water and drying (JP 59-148776A).

Since the acetalization reaction is generally an equilibrium reaction under acidic conditions, the produced SPG undergoes decomposition reaction (reverse reaction). To avoid the decomposition of SPG, the acetalization reaction has been conducted in a solvent having a low dissolving power to SPG so as to allow the produced SPG to rapidly crystallize, thereby shifting the equilibrium to the product side. However, even by the use of the solvent having a low dissolving power to SPG, it is difficult to avoid the decomposition reaction because SPG dissolves in the raw materials to some extent. Other ways for avoiding the decomposition is to decrease the reaction temperature of the SPG synthesis and to use a large amount of solvent. However, these ways are industrially disadvantageous because lowered temperatures make the reaction slow and the use of a large amount of solvent requires large costs for treating waste liquids. Also, in many cases, rapid crystallization of SPG crystals fails to provide SPG crystals having a suitable particle size to allow the easy handling in industrial applications.

To increase the particle size, it has been proposed to produce SPG, for example, by allowing HPA and PE to react in water in the presence of an acid catalyst, neutralizing with alkali, heat-treating the resultant slurry mixture at 120° C. or higher (Japanese Patent 2796130). To reduce the amount of waste water, it has been proposed to produce SPG in a mixed solvent composed of water and an organic solvent immiscible with water in the presence of an acid catalyst (JP 2001-55388A).

In the processes of JP 59-148776A and Japanese Patent 2796130, the amount of waste water including filtrates after recovering SPG, washings, etc. reaches at least about 10 times the weight of SPG produced. The method of increasing the particle size as proposed in Japanese Patent 2796130 requires a re-heating step after the neutralization, to make the process complicated and increase energy consumption. In the process of JP 2001-55388A, although the amount of waste water is reduced, the resultant SPG has a purity as low as 98 to 99% and the used organic solvent should be separated and recovered. In any of the proposed processes, the yield of SPG is as low as 70 to 90 mol % because the raw materials and reaction intermediates remain in the reaction mother liquor after separating SPG crystals, and the environmental load is large in view of disposal of waste water and wastes, and energy consumption.

By reusing the filtrate after recovering SPG in the next run of reaction, the amount of waste water can be reduced and the yield of SPG can be improved. However, impurities are accumulated in the filtrate during its repeated use, to unfavorably cause the lowering of the purity and the reduction of particle size. If the alkali neutralization is conducted after the reaction, a large amount of acid must be required in the next reaction. In addition, the salts produced by the neutralization are accumulated in the mother liquor by its repeated reuse.

Under these circumstances, it has been proposed to directly obtain SPG crystals through the steps of filtration, washing with water, drying, etc. without employing the alkali neutralization. However, SPG produced by these conventional methods decomposes upon heating in the production of derivatives from SPG, to reduce the properties of the products. To avoid these problems, it has been proposed to further purify SPG by crystallization from organic solvents (JP 2000-7678A).

SUMMARY OF THE INVENTION

An object of the present invention is to solve the above problems encountered in prior arts and provide a process for producing high-purity SPG having an increased particle size in high yields. Another object of the invention is to provide a process for producing high-purity SPG which produces less amount of waste water. Still another object of the invention is to provide a process for producing high-purity SPG having a high heat stability.

As a result of extensive research, it has been found that SPG crystals having an increased particle size are produced in high yields by carefully and precisely controlling the raw materials for SPG, the pH value during the reaction, the amount of seed crystals to be added, etc. It has been further found that the heat stability of SPG is improved by the washing with a basic solution. It has been still further found that SPG crystals are easily separated by filtration from the reaction product solution from the above method and the amount of waste water from a plant is reduced by effectively reusing the filtrate. The present invention is based on these findings.

Thus, the present invention is directed to a process for producing a highly pure spiroglycol by a reaction of pentaerythritol and hydroxypivalaldehyde in water in the presence of an acid catalyst, in which (A) a total content of amines and amine salts in hydroxypivalaldehyde is reduced to 1.5% by weight or lower;

(B) seed crystals are added to a reaction system before initiating the reaction and/or during the reaction in an amount from 1.5 to 30% by weight on the basis of a total amount of pentaerythritol, hydroxypivalaldehyde, water, the acid catalyst and the seed crystals, each being fed into the reaction system;

(C) a pH of the reaction system is kept from 0.1 to 4.0 from initiation of the reaction to completion of the reaction; and (D) a sum of a maximum theoretical amount of spiroglycol to be synthesized from pentaerythritol and hydroxypivalaldehyde to be fed into the reaction system and an amount of spiroglycol contained in the seed crystals to be added to the reaction system is controlled within a range from 5 to 35% by weight on the basis of the total amount of pentaerythritol, hydroxypivalaldehyde, water, the acid catalyst and the seed crystals, each being fed into the reaction system.

DETAILED DESCRIPTION OF THE INVENTION

In the process of the present invention, SPG is produced by the reaction of PE and HPA in water in the presence of an acid catalyst. A commercially available PE may be used as-purchased or after purification by distillation or crystallization. A synthesized HPA may be used as-synthesized as long as the total amount of amines and amine salts (for example, trimethylamine and trimethylamine salts of formic acid) is 1.5% by weight or lower. It is preferred to reduce the total amount of amines and amine salts by purification such as crystallization from water. The total amount of amines and amine salts is preferably 0.5% by weight or lower and more preferably 0.1% by weight or lower. If exceeding 1.5% by weight, the amount of the acid catalyst required for the synthesis of SPG increases, the purity of SPG is reduced because of salting-out effect, and the particle size of SPG crystals becomes small. These drawbacks becomes remarkable when the filtered mother liquor is reused. The total amount of amines and amine salts can be industrially reduced to about 0.01% by weight by the crystallization from water.

The molar ratio of HPA to PE (HPA/PE) is from 1.0 to 4.0 and preferably from 1.5 to 2.5. Within the above range, the side reactions of excess HPA is preferably prevented and the highly pure SPG is produced in high yields.

In the process of the invention, seed crystals are added to the reaction system before initiating the reaction and/or during the reaction in an amount of 1.5 to 30% by weight on the basis of the total amount of the raw materials (PE and HPA), water, acid catalyst and seed crystals which are being fed into the reaction system (total feed amount into the reaction system). The seed crystals to be added to the reaction system are mainly made of SPG (SPG content: 90 to 100% by weight). SPG produced by the process of the invention and commercially available SPG may be used as the seed crystals. The particle size of the seed crystals is preferably from 5 to 30 μm and more preferably from 10 to 25 μm, although not limited thereto. The amount of the seed crystals to be added is from 1.5 to 30% by weight, preferably from 1.5 to 10% by weight and more preferably from 1.5 to 5% by weight of the total feed amount into the reaction system. If less than 1.5% by weight, the particle size of SPG is not increased to cause disadvantages of taking longer to filter, cracking the filter cake to make the washing difficult, increasing the liquid content of wet cake, etc. If exceeding 30% by weight, the amount of SPG crystals produced is lowered, to make the efficiency of SPG production poor. The seed crystals may be added to the reaction system either before the initiation of the reaction or during the reaction.

The acid catalyst used in the reaction is preferably a mineral acid such as hydrochloric acid, sulfuric acid, phosphoric acid and nitric acid or an organic acid such as p-toluenesulfonic acid and methanesulfonic acid, although not limited thereto. The amount of the acid catalyst to be used varies depending upon its kind, and is used in an amount so as to keep the pH of the reaction system within 0.1 to 4.0 and preferably within 1.0 to 2.0 from the initiation of reaction to the completion of reaction. If less than 0.1, the tendency of corroding the production equipments increases, although not affecting the yield of SPG. If exceeding 4.0, the reactivity is lowered considerably to reduce the yield of SPG.

In the process of the invention, the raw materials, etc. are fed into the reaction system such that the content of the sum of the maximum theoretical amount of the spiroglycol to be synthesized from PE and HPA to be fed into the reaction system and the amount of spiroglycol contained in the seed crystals to be fed into the reaction system (the sum is hereinafter referred to as "SPG content X") is from 5 to 35% by weight and preferably from 10 to 20% by weight of the total feed amount into the reaction system. The SPG content X corresponds to the concentration of total SPG in the reaction product slurry when 100% of PE is converted into SPG. In a dilute system of an SPG content X of less than 5% by weight, the amount of SPG produced in each run of reaction is small to make the process industrially disadvantageous and the yield of SPG is poor because of low reactivity. If exceeding 35% by weight, the reaction slurry cannot be stirred sufficiently because of an excessively high solid concentration and the purity, yield and particle size of SPG are reduced.

The reaction temperature is preferably from 40 to 105° C. and more preferably from 60 to 95° C. Within the above range, the degradation of HPA is preferably prevented and the highly pure SPG is preferably produced in high yield without taking longer to react.

After charging all of the raw materials, etc. except for HPA into a reactor, the reaction system is heated to a predetermined temperature. Then, the reaction is allowed to proceed by continuously adding HPA or its aqueous solution to the reaction system preferably over 0.5 to 24 h and more preferably over 1 to 6 h. By adding HPA within the above range of time, the reaction proceeds well, the particle sizes of crystals grow into sufficient size, and the highly pure SPG is produced without carrying out the reaction longer.

The terminal point of the reaction varies depending upon the addition time of HPA or its aqueous solution. If the reaction is incomplete, the reaction system may be aged preferably for 0.1 to 48 h, more preferably for 0.1 to 12 h and still more preferably 0.1 to 6 h after the addition of HPA. Since the reaction is an equilibrium reaction, the terminal point of reaction is determined from the consumptions of HPA and PE which are measured by a quantitative analysis of HPA and PE, for example, by an internal standard analysis using gas chromatography.

The reaction product liquid is slurry containing SPG crystals, which are separated by filtration or centrifugal separation. SPG crystals produced in the invention have increased particle size, about 10 to 30 μm. With such increased particle size, the filter cake is free from cracking during the filtration and the liquid content of wet cake is favorably less than 50% by weight.

The reaction mother liquor obtained by separating SPG crystals from the reaction product liquid contains the acid catalyst, unreacted HPA and PE, and intermediate dioxane triol in large amounts. In the process of the invention, preferably 98% by weight or lower, more preferably 50 to 90% by weight of the reaction mother liquor may be reused in the next run of reaction. If the rate of reuse is within the above range, the reduction of SPG purity due to the accumulated impurities in the mother liquor is preferably prevented.

It is preferred to wash the separated SPG crystals with a basic solution because the heat stability of SPG is enhanced. The washing with the basic solution is made, for example, by a method in which SPG crystals and the basic solution are mixed under stirring to form a uniform slurry or a method in which the basic solution is scattered uniformly over SPG crystals by spraying, etc. and then allowed to penetrate into SPG crystals by applying pressure or centrifugal force.

The concentration of the base in the basic solution is preferably from 10 ppm to 50% by weight, more preferably from 0.01 to 15% by weight and still more preferably from 0.01 to 10% by weight. The base is preferably used in an amount of 1.001 to 10 mol per one mole of the acid remaining in separated SPG crystals. The amount of the acid remaining in separated SPG crystals is determined, for example, by an alkali titration of a slurry prepared by adding distilled water to a sampled SPG crystals. Alternatively, if the yield of SPG is known, for example, if the mother liquor is reused, the amount of the acid can be calculated from the weight of the separated SPG crystals and the amount of the charged acid.

After washing, the basic solution used is recovered by filtration or centrifugal separation. It is more preferred to repeat the washing until the pH of the recovered basic solution becomes 8 or more.

The SPG crystals are washed with the basic solution to neutralize the mother liquor held between SPG crystals and the acid on the surface of crystals, and further, to leave an amount of base sufficient for neutralizing the acid that would be generated by the thermal decomposition of SPG.

It is preferred that the liquid content of SPG crystals after washing is the same as the liquid content before washing. The liquid content is usually from 20 to 60% by weight, although varies depending upon particle size and shape of SPG crystals.

The basic solution is prepared by dissolving the base in water and/or an organic solvent. Examples of the organic solvent include methanol, ethanol and acetone. The solvent for the basic solution is preferably the same as that of the washing solution for washing the separated SPG crystals.

Examples of the base include inorganic bases such as lithium carbonate, lithium hydrogencarbonate, magnesium carbonate, sodium hydrogencarbonate, potassium hydrogencarbonate, sodium carbonate, potassium carbonate, sodium hydroxide, potassium hydroxide, sodium phosphate, potassium phosphate, calcium carbonate, calcium hydroxide and barium carbonate; and organic bases such as diethylamine, triethylamine, sodium acetate, potassium acetate, sodium benzoate and potassium benzoate, with the inorganic bases being preferred in view of properties, coloration, odor, etc., of derivatives to be synthesized from SPG.

After washed with the basic solution, SPG crystals may be further washed with water, etc.

The washing with the basic solution may be conducted after the steps of washing with water, drying, etc. By such a washing, the heat stability of SPG is also enhanced. The washing can be made by a method in which SPG and the basic solution are mixed under stirring to form a uniform slurry.

The pH of a 1% methanol solution of SPG thus obtained is preferably from 7.0 to 12.0, more preferably from 7.0 to 10.0 and still more preferably from 7.0 to 8.0. Within the above pH range, the decomposition of SPG due to the remaining acid during heating is prevented. In addition, SPG is prevented from becoming turbid when melted and the generation of odor from the base, particularly from the amine is prevented.

The content of the bases and/or the salts resulted from the reaction between the acid and the base each remaining in SPG obtained finally is preferably from 10 to 1000 ppm, more preferably from 10 to 200 ppm and still more preferably from 10 to 100 ppm. If only the base remains, the content is preferably from 10 to 500 ppm, more preferably from 10 to 200 ppm and still more preferably from 10 to 100 ppm. If both the base and the salt remain or only the salt remains, the content is preferably from 10 to 1000 ppm, more preferably from 10 to 400 ppm and still more preferably from 10 to 200 ppm.

The amount of the base is determined by a neutralization titration of a SPG solution in a solvent such as methanol using hydrochloric acid of known concentration. Although depending upon the kind of base in the basic solution used for washing, the amount of the salt is determined by first measuring the total amount of the base and the salt by an atomic absorption spectroscopic analysis or fluorescent X-ray analysis of alkali metals and alkaline earth metals, and then, subtracting the amount of the base determined by titration from the measured total amount of the base and the salt. If the content of the base and/or the salt is within the above range, the heat stability of SPG is further enhanced and the generation of odor from the base, particularly from the amine is prevented.

The present invention will be described in more detail by referring to the following examples. However, it should be noted that these examples are only illustrative and not intended to limit the invention thereto.

The measurement of SPG purity and the heat resistance test were conducted by the following methods.
(1) Purity of SPG The purity of SPG was determined by gas chromatography (GC) on a methanol solution of SPG.
(2) Heat Resistance Test A test tube was charged with 5 g SPG, purged with nitrogen, and then heated to 210° C. by a block heater. After heating at 210° C. for 3 h, the purity of SPG was determined by GC.

REFERENCE EXAMPLE 1

Synthesis of HPA

In a stream of nitrogen, 33 parts (weight parts, the same applied below) of triethylamine (TEA) was added to a mixture of 595 parts of isobutyl aldehyde (IBAL) and 657 parts of a 37 wt % formalin over 5 min under stirring. After the addition of TEA, the temperature of the reaction liquid reached 65° C. The temperature was then gradually raised from 65° C. and allowed to reach 90° C. after 30 min. After continuing the reaction at 90° C. for 5 min, the reaction liquid was externally cooled to 60° C. to terminate the reaction.

Successively, low-boiling components such as unreacted IBAL, TEA, methanol, etc. were distilled off by distillation at 60 to 70° C. under 53 kPa. After the distillation, the reaction product liquid (crude HPA) was analyzed for its chemical composition by GC. The results are shown below.
HPA: 62.4% by weight
IBAL: 0.26% by weight
Formaldehyde: 2.4% by weight
TEA: 0.31% by weight
Neopentyl glycol: 0.64% by weight
Hydroxypivalic acid neopentyl glycol monoester 2.0% by weight
Isobutyric acid neopentyl glycol monoester 0.18% by weight
Water: 28.5% by weight

REFERENCE EXAMPLE 2

Synthesis of SPG

Into a solution of 48.9 parts of PE in 600 parts of water, was added 5.1 parts of a 35 wt % hydrochloric acid. Then, 146.6 parts of the crude HPA obtained in Reference Example 1 was added dropwise into the resultant mixture over 3.5 h. The pH of the reaction liquid before the initiation of reaction was 1.5, and the reaction temperature was 90° C. After the dropwise addition, the reaction liquid was aged for 3 h while maintaining the temperature at 90° C. The SPG concentration of the resultant reaction slurry at the completion of aging was 15.0% by weight. After the aging, the reaction product solution was separated into wet SPG and 498 parts of reaction mother liquor by solid-liquid separation. The wet SPG was washed with 450 parts of water and then dried, to obtain 82.0 parts of SPG crystals. The yield of SPG was 75 mol % based on the charged PE, and the purity of SPG crystals was 99.2% by weight. The average particle size of SPG crystals was 8 μm when measured on a water dispersion of SPG crystals by using a wet particle size distribution analyzer after exposing the water dispersion to ultrasonic wave for 10 min. During the solid-liquid separation by filtration through a glass filter under reduced pressure, the cake cracked. The liquid content of SPG cake immediately after the filtration was 52% by weight.

EXAMPLE 1

Synthesis of SPG from Crude HPA

Into a solution of 48.9 parts of PE in 600 parts of water, were added 5.1 parts of a 35 wt % hydrochloric acid and 13 parts of SPG crystals obtained in Reference Example 2 as seed crystals (1.6% by weight of the total feed amount into the reaction system). Then, 146.6 parts of the crude HPA obtained in Reference Example 1 was further added dropwise over 3.5 h. The pH of the reaction liquid at the initiation of reaction was 1.5, and the reaction temperature was 90° C. After the dropwise addition, the reaction liquid was aged for 3 h while maintaining the temperature at 90° C. The SPG content X was 15.0% by weight. The pH of the reaction production solution at the completion of reaction was 1.8. After the aging, the reaction product solution was separated into wet SPG and 498 parts of reaction mother liquor by solid-liquid separation. The wet SPG was washed with 450 parts of water and then dried, to obtain 96.2 parts of SPG crystals. The yield of SPG was 76.1 mol % based on the charged PE, and the purity of SPG crystals was 99.3% by weight. The average particle size of SPG crystals was 12 μm when measured on a water dispersion of SPG crystals by using a wet particle size distribution analyzer after exposing the water dispersion to ultrasonic wave for 10 min. The amount of waste water (reaction mother liquor+recovered washings+recovered water in drying) was 1123.8 parts. During the solid-liquid separation by filtration through a glass filter under reduced pressure, no crack occurred on the cake. The liquid content of SPG cake immediately after the filtration was 37% by weight.

First Recycling Reaction

Next, a first recycling reaction was performed in the same manner as in the above synthesis except for using 560 parts of the reaction mother liquor (80% by weight of the whole amount), 40 parts of water, 2.7 parts of a 35 wt % hydrochloric acid and 131.4 parts of crude HPA. The yield of dried SPG was 93.0 mol % based on PE freshly added (the same applied below), and the purity was 99.4% by weight. The average particle size after exposed to ultrasonic wave was 10 μm. During the solid-liquid separation by filtration through a glass filter under reduced pressure, no crack occurred on the cake. The liquid content of SPG cake immediately after the filtration was 38% by weight.

Second and Subsequent Recycling Reactions

The above procedure was repeated to perform the recycling reactions up to 10 cycles. The yield of SPG was 90.0 mol %, the purity was 99.3% by weight, and the particle size after exposed to ultrasonic wave was 11 μm, each in average of second to tenth recycling reactions. The amount of waste water was 750 parts in average. During the solid-liquid separation by filtration through a glass filter under reduced pressure, no crack occurred on the cake. The liquid content of SPG cake immediately after the filtration was 45% by weight in average.

EXAMPLE 2

Purification of HPA

A complete mixture was prepared at 55° C. by adding 2505 parts of water into 835 parts of the crude HPA obtained in Reference Example 1. The mixture was gradually cooled from 55° C. to 32° C. over 5 h under stirring and then kept at 32° C. for one hour. The resultant crystals were separated by solid-liquid separation using a top-discharge centrifugal separator and then washed with water, to obtain HPA having a purity of 96.5% by weight in 60% recovery. The water content was 12% by weight and the remaining TEA content was 0.01% by weight.

Synthesis of SPG from Purified HPA

Into a solution of 95 parts of PE in 1200 parts of water, were added 5 parts of p-toluenesulfonic acid (PTSA) and 26 parts of SPG crystals obtained in Reference Example 2 as seed crystals (1.7% by weight of the total feed amount into the reaction system). Then, an aqueous solution of the purified HPA prepared by dissolving 160 parts of the purified HPA in 65 parts of water under heating at 80° C. was further added dropwise over 3.5 h. The SPG content X was 14.8% by weight. The pH of the reaction liquid at the initiation of reaction was 1.8, and the reaction temperature was 90° C. After the dropwise addition, the reaction liquid was aged for 2 h while maintaining the temperature at 90° C. The pH of the reaction production solution at the completion of reaction was 1.8. After the aging, the reaction product solution was separated into wet SPG and 1240 parts of reaction mother liquor by solid-liquid separation. The wet SPG was washed with 460 parts of water and then dried, to obtain 147 parts of SPG crystals. The yield of SPG was 56.8 mol % based on the charged PE, and the purity of SPG crystals was 99.9% by weight when analyzed by GC. The average particle size of SPG crystals was 23 μm when measured on a water dispersion of SPG crystals by using a wet particle size distribution analyzer after exposing the water dispersion to ultrasonic wave for 10 min. The amount of waste water (reaction mother liquor+recovered washings+recovered water in drying) was 1780 parts. During the solid-liquid separation by filtration through a glass filter under reduced pressure, no crack occurred on the cake. The liquid content of SPG cake immediately after the filtration was 37% by weight.

First Recycling Reaction

Next, a first recycling reaction was performed in the same manner as in the above synthesis except for making 1200 parts of the reaction mother liquor (85% by weight of the whole amount) and 95 parts of PE into a solution under heating and using 0.7 part of PTSA and 240 parts of the aqueous solution of the purified HPA. The yield of dried SPG was 96.5 mol % and the purity was 99.8% by weight. The average particle size after exposed to ultrasonic wave was 22 μm. During the solid-liquid separation by filtration through a glass filter under reduced pressure, no crack occurred on the cake. The liquid content of SPG cake immediately after the filtration was 37% by weight.

Second Recycling Reaction

Next, a second recycling reaction was performed in the same manner as in the first recycling reaction except for using 1100 parts of the reaction mother liquor (83% by weight of the whole amount) and 100 parts of water. The yield of dried SPG was 94.6 mol % and the purity was 99.8% by weight. The average particle size after exposed to ultrasonic wave was 22 μm. During the solid-liquid separation by filtration through a glass filter under reduced pressure, no crack occurred on the cake. The liquid content of SPG cake immediately after the filtration was 37% by weight.

Third and Subsequent Recycling Reactions

The above procedure was repeated to perform the recycling reactions up to 10 cycles. The yield of SPG was 94.0 mol %, the purity was 99.7% by weight, and the particle size after exposed to ultrasonic wave was 20 μm or more, each in average of third to tenth recycling reactions. The amount of waste water was 584 parts in average. During the solid-liquid separation by filtration through a glass filter under reduced pressure, no crack occurred on the cake. The liquid content of SPG cake immediately after the filtration was 42% by weight in average.

COMPARATIVE EXAMPLE 1

The recycling reactions were conducted in the same manner as in Example 1 up to 10 cycles except for using the crude HPA obtained in Reference Example 1 as the raw material and omitting the addition of seed crystals. The purity of SPG was 99.0% by weight, the yield was 88.0 mol % and the particle size after exposed to ultrasonic wave was 6 μm, each in average of first to tenth recycling reactions. During the solid-liquid separation by filtration through a glass filter under reduced pressure, the crack of cake occurred. However, the filtration, washing with water and drying were made as in Example 1 to obtain SPG crystals. The liquid content of SPG cake immediately after the filtration was 52% by weight in average.

COMPARATIVE EXAMPLE 2

The recycling reactions were conducted in the same manner as in Example 1 up to 10 cycles except for using the crude HPA obtained in Reference Example 1 as the raw material and adding seed crystals in an amount of 0.5% by weight of the total feed amount into the reaction system. The purity of SPG was 99.2% by weight, the yield was 80.0 mol % and the particle size after exposed to ultrasonic wave was 7 μm, each in average of first to tenth recycling reactions. During the solid-liquid separation by filtration through a glass filter under reduced pressure, the crack of cake occurred. However, the filtration, washing with water and drying were made as in Example 1 to obtain SPG crystals. The liquid content of SPG cake immediately after the filtration was 52% by weight in average.

COMPARATIVE EXAMPLE 3

The synthesis of SPG was conducted in the same manner as in Example 1 except for using the crude HPA obtained in Reference Example 1 as the raw material and adjusting the pH to 4.5 during the synthesis of SPG. Although the purity was 99.5% by weight, the yield was as extremely low as 40.0 mol %. The particle size after exposed to ultrasonic wave was 10 μm.

COMPARATIVE EXAMPLE 4

A suspension of 50 parts of PE in a mixture of 180 parts of water and 18 parts of xylene was heated to 60° C., to which 124 parts of the crude HPA obtained in Reference Example 1 and 9 parts of a 50 wt % sulfuric acid were simultaneously added over 2 h. After stirring for 12 h while keeping the temperature at 60° C., the mixture was neutralized with a 48 wt % sodium hydroxide aqueous solution. The resultant slurry mixture was filtered under reduced pressure and the separated solid was washed with water and dried, to obtain 99.5 parts of SPG. The yield was 89 mol %, the purity was 98% by weight, and the particle size after exposed to ultrasonic wave was 9 μm. During the solid-liquid separation by filtration through a glass filter under reduced pressure, the crack of cake occurred. However, the filtration, washing with water and drying were made as in Example 1 to obtain SPG crystals. The liquid content of SPG cake immediately after the filtration was 60% by weight.

COMPARATIVE EXAMPLE 5

A mixture of 306 parts of the crude HPA obtained in Reference Example 1 and 1116 parts of an aqueous solution containing 116 parts of PE was stirred and made into a uniform solution under heating at 60° C. To the resultant solution was added 22 parts of a 98 wt % sulfuric acid at once and the reaction was allowed to proceed for 6 h at 60° C. After the reaction, the reaction product solution was neutralized with a 48 wt % sodium hydroxide aqueous solution. Through filtration, washing and drying, 207 parts of SPG were obtained. The yield was 80 mol %, the purity was 93% by weight, and the particle size after exposed to ultrasonic wave was 8 μm. During the solid-liquid separation by filtration through a glass filter under reduced pressure, the crack of cake occurred. However, the filtration, washing with water and drying were made as in Example 1 to obtain SPG crystals. The liquid content of SPG cake immediately after the filtration was 60% by weight.

COMPARATIVE EXAMPLE 6

The synthesis of SPG was conducted in the same manner as in Example 1 except for using the crude HPA obtained in Reference Example 1 as the raw material and regulating the initial charges of water, seed crystals and acid so that the SPG content X was 40% by weight. The addition amount of seed crystals was 1.6% by weight of the total feed amount into the reaction system and the pH at the initiation of reaction was 1.5. Although the slurry became difficult to be sufficiently stirred in the course of the reaction because of an excessively high concentration, the reaction was allowed to continue. The purity of SPG was 86.5% by weigh and the yield was 65.0 mol %. During the solid-liquid separation by filtration through a glass filter under reduced pressure, the crack of cake occurred. However, the filtration, washing with water and drying were made as in Example 1 to obtain SPG crystals.

COMPARATIVE EXAMPLE 7

In the same manner as in Reference Example 1, a crude HPA having a remaining TEA content of 5% by weight was obtained. The synthesis of SPG and the recycling reactions up to 10 cycles were conducted in the same manner as in Example 1 except for regulating the amount of acid catalyst so that the pH at the completion of reaction was 1.8 (acid catalyst: 12.7 g of hydrochloric acid for the synthesis of SPG and 8.6 g of hydrochloric acid for the recycling reactions). The purity of SPG was 97.8% by weight, the yield was 80.0 mol % and the particle size after exposed to ultrasonic wave was 5 μm, each in average of first to tenth recycling reactions. During the solid-liquid separation by filtration through a glass filter under reduced pressure, the crack of cake occurred. However, the filtration, washing with water and drying were made as in Example 1 to obtain SPG crystals. The liquid content of SPG cake immediately after the filtration was 60% by weight in average.

TABLE 1

| | Purification of HPA | Seed crystals | Number of recycling | Yield based on PE (%) | Purity (%) | Average particle size (μm) | Liquid content (%) | Crack of cake | Remarks |
|---|---|---|---|---|---|---|---|---|---|
| Reference Example | | | | | | | | | |
| 2 | none | none | 0 | 75.0 | 99.2 | 8 | 52 | occurred | none |
| Examples | | | | | | | | | |
| 1 | none | added | 0 | 76.1 | 99.3 | 12 | 37 | none | |
| | none | added | 1 | 93.0 | 99.4 | 10 | 38 | none | |
| | none | added | 2-10 | 90.0 | 99.3 | 11 | 45 | none | |
| 2 | purified | added | 0 | 56.8 | 99.9 | 23 | 37 | none | |
| | purified | added | 1 | 96.5 | 99.8 | 22 | 37 | none | |
| | purified | added | 2 | 94.6 | 99.8 | 22 | 37 | none | |
| | purified | added | 3-10 | 94.0 | 99.7 | 20 | 42 | none | |
| Comparative Examples | | | | | | | | | |
| 1 | none | none | 1-10 | 88.0 | 99.0 | 6 | 52 | occurred | |
| 2 | none | slightly added | 1-10 | 80.0 | 99.2 | 7 | 52 | occurred | |
| 3 | none | added | 0 | 40.0 | 99.5 | 10 | — | none | pH: 4.5 |
| 4 | none | none | 0 | 89.0 | 98.0 | 9 | 60 | occurred | water/xylene mixed solvent |
| 5 | none | none | 0 | 80.0 | 93.0 | 8 | 60 | occurred | |
| 6 | none | added | 0 | 65.0 | 86.5 | — | — | occurred | SPG content X: 40 wt % |
| 7 | none | added | 1-10 | 80.0 | 97.8 | 5 | 60 | occurred | HPA contained 5% amines |

EXAMPLE 3

Basic Solution Treatment 1

Into a solution of 48.9 parts of PE in 600 parts of water, were added 5.1 parts of a 35 wt % hydrochloric acid and 13 parts of SPG crystals obtained in Reference Example 2 as seed crystals (1.6% by weight of the total feed amount into the reaction system). Then, 146.6 parts of the crude HPA obtained in Reference Example 1 was further added dropwise over 3 h. The pH of the reaction liquid at the initiation of reaction was 1.5, and the reaction temperature was 90° C. After the dropwise addition, the reaction liquid was aged for 2 h while maintaining the temperature at 90° C. The SPG content X was 15.0% by weight. The pH of the reaction production liquid at the completion of reaction was 1.8. After the aging, the reaction product liquid was solid-liquid separated by filtration under reduced pressure to obtain SPG crystals. SPG crystals were washed by spraying 50 parts of a 1% sodium carbonate aqueous solution. The pH of the recovered basic solution was 8.5. Successively, SPG crystals were washed with 280 parts of water and then dried, to obtain 96.0 parts of SPG crystals. The yield of SPG was 75.9 mol % based on the initially charged PE and the purity was 99.3% by weight. The pH of a 1% methanol solution of SPG was 7.3 and the remaining salt content in SPG was 16 ppm. The results of heat resistance test are shown in Table 2.

EXAMPLE 4

Basic Solution Treatment 2

The procedure of Example 3 was repeated except for washing SPG crystals with 5000 parts of a 10 ppm sodium carbonate aqueous solution after the solid-liquid separation by filtration under reduced pressure. The pH of the recovered basic solution was 8.0. The yield of SPG was 75.7 mol % based on the initially charged PE and the purity was 99.3% by weight. The pH of a 1% methanol solution of SPG was 7.3 and the remaining salt content in SPG was 13 ppm. The results of heat resistance test are shown in Table 2.

EXAMPLE 5

Basic Solution Treatment 3

The procedure of Example 3 was repeated except for washing SPG crystals with 1.0 part of a 50% sodium hydroxide aqueous solution after the solid-liquid separation by filtration under reduced pressure. The pH of the recovered basic solution was 12. The yield of SPG was 75.7 mol % based on the initially charged PE and the purity was 99.3% by weight. The pH of a 1% methanol solution of SPG was 7.5 and the remaining salt content in SPG was 18 ppm. The results of heat resistance test are shown in Table 2.

COMPARATIVE EXAMPLE 8

The procedure of Example 3 was repeated except for omitting the washing of SPG crystals with a basic solution after the solid-liquid separation by filtration under reduced pressure. The pH of the recovered basic solution was 2.5. The yield of SPG was 75.8 mol % based on the initially charged PE and the purity was 99.3% by weight. The pH of a 1% methanol solution of SPG was 6.5. The results of heat resistance test are shown in Table 2.

EXAMPLE 6

Basic Solution Treatment 4

A 2-L three-necked flask equipped with a stirrer and a reflux condenser was charged with 400 parts of SPG prepared by the method of Comparative Example 8 and 1598 parts of water. Separately, a part of SPG prepared by the method of Comparative Example 8 was sampled and mixed with distilled water to prepare a slurry, and the amount of acid in SPG crystals was determined by alkali titration. After 2 parts of sodium hydrogencarbonate corresponding to 1.2 molar times the amount of the acid was added to the flask, the contents were stirred for 2 h at 90° C. and then filtered under reduced pressure. The pH of the recovered basic solution was 8.9. Separated SPG crystals were washed with water and dried. The purity of SPG was 99.3% by weight and the recovery of SPG was 99.5% by weight. The pH of a 1% methanol solution of SPG was 7.3 and the remaining salt content in SPG was 13 ppm. The results of heat resistance test are shown in Table 2.

COMPARATIVE EXAMPLE 9

A 2-L three-necked flask equipped with a stirrer and a reflux condenser was charged with 400 parts of SPG prepared by the method of Comparative Example 8 and 1600 parts of water, and the contents were stirred for 2 h at 90° C. and then filtered under reduced pressure. The pH of the recovered filtrate was 5.8. Separated SPG crystals were washed with water and dried. The purity of SPG was 99.3% by weight and the recovery of SPG was 99.6% by weight. The pH of a 1% methanol solution of SPG was 6.8. The results of heat resistance test are shown in Table 2.

COMPARATIVE EXAMPLE 10

A 2-L three-necked flask equipped with a stirrer and a reflux condenser was charged with 160 parts of SPG prepared in Comparative Example 8 and 1600 parts of methanol, and the contents were heated to 60° C. to prepare a complete solution. The solution was gradually cooled to 40° C. over 6 h. The crystals were separated by filtration under reduced pressure, washed with methanol and then dried, to obtain SPG crystals. The purity of the SPG was 100% by weight and the recovery of SPG was 70% by weight. The pH of a 1% methanol solution of SPG was 7.3 and the remaining salt content in SPG was zero. The results of heat resistance test are shown in Table 2.

COMPARATIVE EXAMPLE 11

Into a solution of 49 parts of PE in 600 parts of water placed in a reactor, 5.7 parts of a 35% hydrochloric acid was added. Then, 147 parts of a solution of crude HPA was added dropwise over 5 h. The reaction temperature was 70° C. After the dropwise addition, the reaction product liquid was aged for 3 h while maintaining the temperature at 70° C. After the aging, the reaction product liquid was cooled to 40° C. over 2 h and then neutralized with a 25% sodium hydroxide aqueous solution until the pH reached 6.5. Through solid-liquid separation, washing with water and drying, 91 parts of SPG were obtained. The yield of SPG was 83 mol % based on the initially charged PE and the purity was 99.5% by weight. The results of heat resistance test are shown in Table 2.

TABLE 2

| | Purity of SPG | | | |
|---|---|---|---|---|
| | Before test wt % | After test wt % | Decomposed SPG * wt % | Washing |
| Examples | | | | |
| 3 | 99.3 | 91.6 | 7.7 | washed |
| 4 | 99.3 | 92.2 | 7.1 | washed |
| 5 | 99.3 | 91.5 | 7.8 | washed |
| 6 | 99.3 | 93.2 | 6.1 | washed |
| Comparative Examples | | | | |
| 8 | 99.3 | 83.3 | 16 | none |
| 9 | 99.3 | 87.7 | 11.6 | none |
| 10 | 100 | 90.5 | 9.5 | none |
| 11 | 99.5 | 90.5 | 9 | none |

*Decomposed SPG = Purity(before test) − Purity(after test)

The results of the heat resistance tests show that SPG that was not washed with the basic solution tends to be decomposed.

SPG is a polyhydric alcohol containing a cyclic acetal structure in its molecule, and is useful as an intermediate product or a monomer for the production of polymer materials such as polycarbonates, polyesters, polyacrylates, polyurethanes, polyether polyols and epoxy resins, and also useful as raw materials for adhesives, plasticizers, resin stabilizers, lubricants, etc.

Highly pure SPG crystals produced according to the present invention have an increased particle size and so easy to handle. Since the amount of waste water is reduced, the process of the invention significantly reduces the environmental load. The process of the invention further provides SPG with an improved heat stability. For example, by using SPG produced according to the invention in the esterification reaction of SPG and a higher carboxylic acid, the reduction in purity of products due to decomposition is avoided.

What is claimed is:

1. A process for producing 3,9-bis(1,1-dimethyl-2-hydroxyethyl)-2,4,8,10-tetraoxaspiro[5.5]undecane (spiroglycol), comprising reacting pentaerythritol and hydroxypivalaldehyde in water in the presence of an acid catalyst, wherein:
   (A) a total content of amines and amine salts in the hydroxypivalaldehyde is reduced to 0.31% by weight or lower;
   (B) seed crystals are added to a reaction system before initiating the reaction and/or during the reaction in an amount from 1.5 to 30% by weight on the basis of a total amount of pentaerythritol, hydroxypivalaldehyde, water, the acid catalyst and the seed crystals, each being fed into the reaction system;
   (C) a pH of the reaction system is kept from 0.1 to 4.0 from initiation of the reaction to completion of the reaction; and
   (D) a sum of a maximum theoretical amount of spiroglycol to be synthesized from pentaerythritol and hydroxypivalaldehyde to be fed into the reaction system and an amount of spiroglycol contained in the seed crystals to be added to the reaction system is controlled within a range from 5 to 35% by weight on the basis of the total amount of pentaerythritol, hydroxypivalaldehyde, water, the acid catalyst and the seed crystals, each being fed into the reaction system.

2. The process according to claim 1, wherein 50-98% by weight of a reaction mother liquor obtained by separating spiroglycol crystals from a reaction product liquid is reused in the next reaction.

3. The process according to claim 1, wherein the hydroxypivalaldehyde is added to the reaction system over 0.5 to 24 h.

4. The process according to claim 1, wherein the seed crystals are mainly made of spiroglycol.

5. The process according to claim 1, wherein the amines and amine salts are triethylamine and triethylamine salt of formic acid.

6. The process according to claim 1, wherein crystals of spiroglycol are washed with a basic solution after being separated from a reaction production liquid.

7. The process according to claim 6, wherein a 1% methanol solution of the spiroglycol after being washed with the basic solution has a pH of 7.0 to 12.0.

8. The process according to claim 6, wherein a content of bases and/or salts resulting from a reaction of acids and the bases remaining in the spiroglycol after being washed with the basic solution and dried is 10 to 1000 ppm.

9. The process according to claim 6, wherein the basic solution is a solution of an inorganic base in water and/or an organic solvent.

10. The process according to claim 6, wherein a concentration of the base in the basic solution is 10 ppm to 50% by weight.

11. The process according to claim 1, wherein said total content of amines and amine salts in the hydroxypivalaldehyde is reduced to 0.1% by weight or lower.

12. The process according to claim 1, wherein in the step (D), a sum of a maximum theoretical amount of spiroglycol to be synthesized from pentaerythritol and hydroxypivalaldehyde to be fed into the reaction system and an amount of spiroglycol contained in the seed crystals to be added to the reaction system is controlled within a range of from 10 to 20% by weight on the basis of the total amount of pentaerythritol, hydroxypivalaldehyde, water, the acid catalyst and the seed crystals, each being fed into the reaction system.

* * * * *